United States Patent [19]

Burl et al.

[11] 4,361,807
[45] Nov. 30, 1982

[54] NUCLEAR MAGNETIC RESONANCE SYSTEMS

[75] Inventors: Michael Burl, Iver; Ian R. Young, Sunbury-on-Thames, both of England

[73] Assignee: Picker International Limited, Wembley, England

[21] Appl. No.: 176,913

[22] Filed: Aug. 11, 1980

[30] Foreign Application Priority Data

Aug. 10, 1979 [GB] United Kingdom ............... 7927971

[51] Int. Cl.$^3$ ............................................. G01N 27/00
[52] U.S. Cl. ..................................... 324/309; 324/310
[58] Field of Search ........................ 324/300, 309, 310

[56] References Cited

U.S. PATENT DOCUMENTS

| 3,048,772 | 8/1962 | Saunders et al. | 324/310 |
| 4,021,726 | 6/1977 | Garroway et al. | 324/305 |
| 4,070,611 | 1/1978 | Ernst | 324/309 |
| 4,115,730 | 9/1978 | Mansfield | 324/309 |

OTHER PUBLICATIONS

Phosphorus Nuclear Magnetic Resonance Studies of Heat Physiology, Donald P. Hollis et al., May 1977, 12 pages.

*Primary Examiner*—Michael J. Tokar
*Attorney, Agent, or Firm*—Fleit & Jacobson

[57] ABSTRACT

The invention provides an investigation of chemical shift for an element, for example phosphorus, in a region of a body, in one example resonance is preferentially in a line in a slice of the body. Frequency dispersion down the line is produced by a pulsed field having a switched gradient so that the frequency distribution is in steps. This allows a chemical dispersion in each limited region of the line without overlap with adjacent regions. The measured FID signals are Fourier transformed to give a spatial and chemical analysis of the line.

Alternatively resonance is excited in a slice and lines selected by a pulsed gradient which gives chemical dispersion as well as spatial dispersion between the lines after Fourier Transformation. This is repeated for many different directions of the pulsed gradient to allow analysis of a chemical line by convolution techniques to give a picture for the slice.

14 Claims, 13 Drawing Figures

NUCLEAR MAGNETIC RESONANCE SYSTEMS

The present invention relates to systems for providing, by nuclear magnetic resonance (NMR), distributions of chemicals in a selected region of a body. In particular, but not exclusively, it relates to measuring distributions of phosphorus. The examination is particularly applicable also to use for medical investigation of patients.

Phosphorus ($^{31}$P) exists in low concentrations in the human body. It has a small nuclear magnetic movement and has a gyromagnetic ratio of 17.43 MH$_z$ Tesla$^{-1}$ (compared with 42.6 MH$_z$ T$^{-1}$ for the protons for which NMR studies are normally used).

Techniques have been described for obtaining proton images of bodies. However because of the low concentrations mentioned, times in the range 12-1200 minutes would be required to obtain such images for $^{31}$P, for a pixel size 40×40×40 mm and a signal to noise ratio of 14. It is therefore perhaps not the preferred approach to attempt such images.

It is an object of this invention to provide an alternative method and apparatus for investigating phosphorus and other chemicals in the body of NMR.

According to the invention there is provided a method of determining the distribution, in a body, of chemicals including a chosen element, for example phosphorus, the method including the steps of: exciting resonance for said element preferentially in a region in said body; applying a magnetic field having a gradient in said region to introduce a frequency dispersion in said resonance, said gradient being switched to provide free induction decay signals, in the form of a line spectrum of a Fourier series; measuring the free induction decay signals; and Fourier transforming the free induction decay signals to provide the chemical shifts for said element for a plurality of individual parts of said region as dispersed spectra around the lines of said first mentioned spectrum.

According to another aspect of the invention there is provided a method of investigating the distribution of chemicals in a body the method including the steps of: applying magnetic fields to cause resonance preferentially in a region of said body at a frequency appropriate to a chosen element; applying a switched magnetic field having a gradient along said region to produce dispersion in said resonance, the timing of the field being such that the region is effectively divided into a plurality of smaller regions, the nuclei of the chosen element in each region resonating within a unique frequency band and dispersion in that band representing a chemical shift to be determined; sensing free induction decay and rephasing signals emitted by the nuclei as the field gradient is switched; sampling the free induction decay and rephasing signals and Fourier Transforming the samples so that the frequencies in the samples are dispersed, the dispersion being indicative of both spatial and chemical shift, the gradient being of sufficient amplitude that the frequency shift, is larger than the chemical shift by an amount sufficient to avoiid ambiguity.

The invention embraces an apparatus for implementing the method of the two preceding paragraphs.

In order that the invention may be clearly understood and readily carried into effect it will now be described by way of example with reference to the accompanying drawings of which.

Biochemical studies (for example as described in the paper by Hollis et. el.: J. Mag. Res 29, 319 (1978)) have been performed on perfused animal hearts by monitoring the relative abundance of various chemicals containing $^{31}$P. The various chemicals are distinguished by the chemical shift of the $^{31}$P lines. These studies have shown strong correlation between the relative strengths of the different $^{31}$P lines and various heart conditions. The chemical shifts are of the order of 10-20 ppm.

NMR imaging systems proposed can provide, in central regions generally at least as large as the heart, field uniformities around 1 ppm and it is proposed to use these systems to examine the human heart in vivo. This is equivalent to using the imaging system as a large scale spectrometer since what is to be measured is the spectrum given by the chemical shift of the $^{31}$P lines.

The chemical shift between resonance lines arises because atoms of the same element attached at various sites on the same molecule or to different molecules find themselves in different micro-fields, i.e. the fields due to neighbouring atoms of the same or other species. These fields are necessarily small and hence the shifts are also small, 10 ppm being a relatively large shift.

Figure 1:
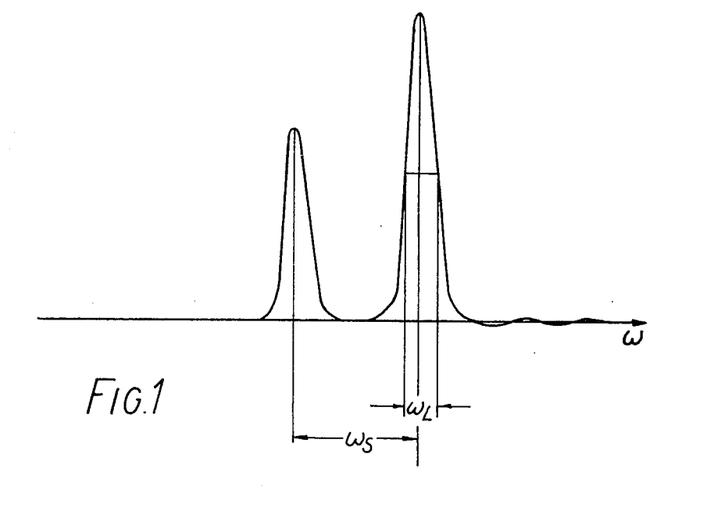
FIG. 1 shows a chemical shift between two resonance lines of the same element.

FIG. 1 shows an example of two lines separated by a shift $W_s$. Each line has a line width $W_L$. It should be noted that there is no reason for each line to have the same line width; independent lines have their own independent values of relaxation times $T_1$ and $T_2$, reflecting their differing chemical environments.

Figure 2:
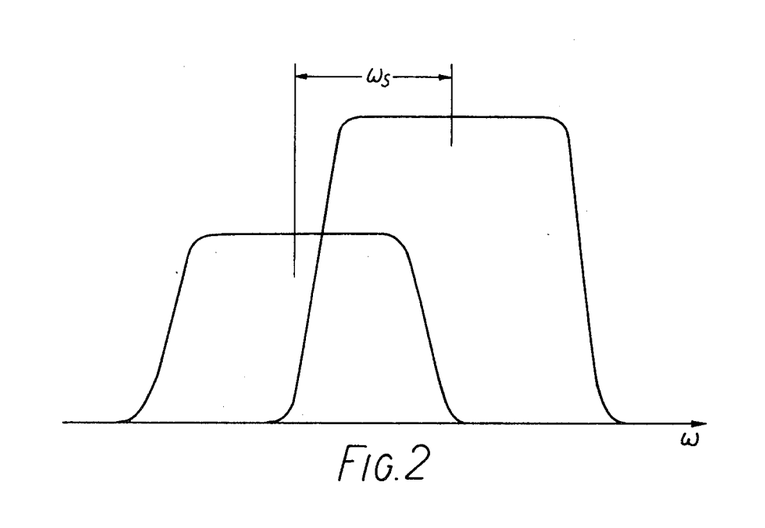
FIG. 2 shows two such lines in the presence of an excessively strong gradient.

If it is desired to perform imaging studies by any means, it is necessary to apply field gradients of some kind to introduce spatial encoding of the NMR signal. FIG. 2 shows the effect of too strong a gradient; it can be seen that each line is dispersed by the bandwidth of the gradient field and the two broadened lines overlap. The spectrum is degenerate; it is impossible uniquely to assign the origin of a given region of the spectrum. This is the normal situation in proton imaging in which chemical shifts of the proton lines are ignored.

Figure 3:
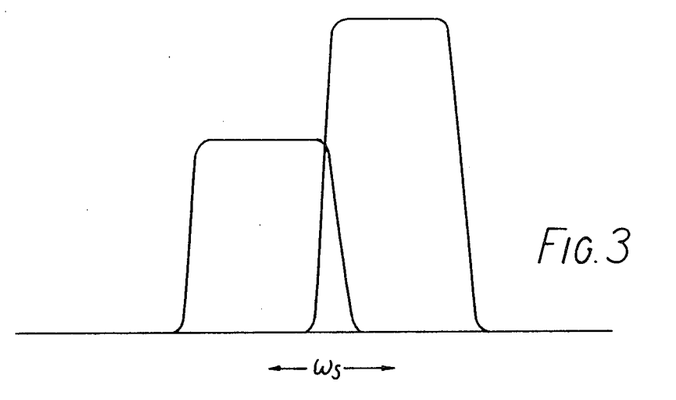
FIG. 3 shows the same lines in the presence of a gradient of an intermediate strength allowing sufficient resolution.

FIG. 3 shows that to avoid degeneracy the gradient field bandwidth must be restricted to less than the chemical shift of the two lines. The maximum number of pixels or strips that can be resolved is simply $W_s/W_L$.

The method which it is proposed to apply in one embodiment of the invention is in effect the same as that used for proton imaging in that it is proposed to isolate a cross-sectional slice of the body and then cause resonance, at a frequency appropriate to $^{31}$P (i.e. 1.743 MH$_z$ for a 0.1T field) preferentially in a line or strip of that slice.

The first requirement for this is to create a large uniform and steady magnetic field, which can be called Bo, to define the equilibrium spin polarization axis of the molecules in a direction which can be identified as z. This will probably be axial of the patient.

A linear magnetic field gradient $G_z$ is applied, where $G_z=(\partial B_z/\partial z)$. Simultaneously there is applied an RF ($B_1$) field. The $B_1$ field is tailored to saturate all of the spins except those in the selected slice, using a technique developed by Mansfield and described in U.S. Pat. No. 4,021,726. Following this there is applied another gradient $G_x=(\partial B_z/\partial x)$ where x is one of two orthogonal directions (x and y) in the slice. The effect of the Gx gradient is to provide a dispersion of Larmor frequencies in the x direction so that each of a plurality of adjacent strip perpendicular to the x-direction has Larmor frequencies within a respective small range about a mean for the strip. Selection of a strip is then by application of a 90° $B_1$ pulse as is well known in NMR at the mean Larmor frequency for the chosen strip. This then excites all of the molecules in the strip preferentially over the other molecules in the slice. When the molecules have been excited a free induction decay (free induction decay) signal of known form results. It may be noted that the effect of saturating molecules outside the selected slice is that these molecules will not respond to the further fields; the line selection is then by that method which has been previously proposed for slice selection in NMR imaging. A gradient $$Gy\left(Gy = \frac{\partial B_z}{\partial y}\right),$$

where y is the direction along the line, can then be applied to disperse the frequencies along the line.

Figure 4A:
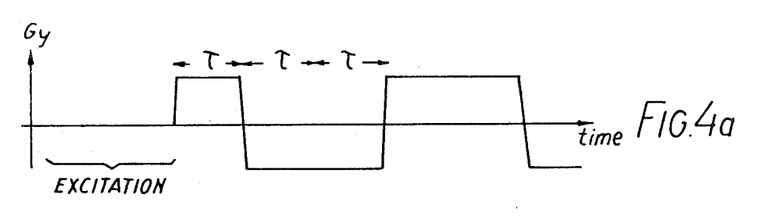
FIG. 4a shows the form of the gradient field along a selected strip.
Figure 4B:
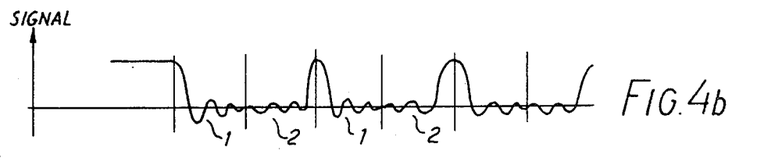
FIG. 4b shows the resulting FID and rephasing signals.

It is however also desired to accommodate the chemical shift which is to be measured. For that reason the Gy field gradient is switched as shown in FIG. 4a. The result of this switching is that there is produced a spin echo signal each time the gradient is reversed, as shown in FIG. 4b. The free induction decay signal, instead of being a continuous spectrum, is now a line spectrum of a Fourier series (because of the repetitive nature of the switching). In effect this means that instead of there being a continuous gradation of Larmor frequency down the strip, as is normally produced by a steady Gy gradient, the frequency dispersion is in steps. The strip is thus effectively divided into a plurality of small elements each at a respective Larmor frequency. However, adjacent elements are not at adjacent frequencies but are spaced.

The reason that this spacing is desired that the chemical shift to be measured (about 50-60 p.p.m. for phosphorous) provides a further small frequency dispersion so that each small element has in fact a spectrum of frequencies and not a single value. The spacing (typically 100 p.p.m.) produced by the stepped Gy gradient allows this chemical dispersion without causing frequency overlap between adjacent elements so that the chemical information is not lost. In practice quite a large spacing is required to accommodate the chemical shift and is not likely that more than six elements can be resolved in a line.

Turning to FIG. 4a again it can be seen that the Gy gradient can be considered to be in small steps of duration $\tau$ and that each one of these gives an FID signal (1) or a rephasing signal (2) which is the mirror image of an FID.

For processing each rephasing signal is mirror imaged to take the same form as free induction decay.

The sampled data comprises information for both the spatial (y direction) dispersion and the chemical shift dispersion and can be Fourier transformed to give the chemical analysis for each element of the strip. The procedure is to be repeated with appropriately different fields to examine other strips. Reversal of the rephasing signals is a relatively straight-forward operation since each free induction decay or rephasing signal is usually digitised and stored in digital form before Fourier transformation. It is merely necessary to withdraw the rephasing signal from storage in the reverse order to the free induction decay signals.

The procedure is repeated with different Gx gradients to select different strips so as to provide chemical information for a matrix of elements. It has previously been mentioned that in order to accommodate the chemical information it is, in practice, only possible to obtain low spatial resolution giving typically 6×6 or even 4×4 matrices. The chemical information may be displayed in different manners as desired. It is simple, for such a small matrix, to separate the lines for each element and to provide a different picture for each chemical line resolved.

Essentially the same procedure may be applied to other imaging techniques to allow chemical dispersion. That described hereinbefore involves strip excitation but another suitable method involves adapting the slice excitation methods such as described in our co-pending patent application No. 22291/78.

In that procedure the large uniform and steady Bo field is applied as before. Similarly the Gz field gradient is applied but the RF ($B_1$) field applied with it is in this method a 90° pulse so that a substantially planar slice of the patient is excited. Preferably this is followed by a further Gz gradient pulse to rephase the spins across the slice (as described in said application No. 22291/78). Finally a $G_R$ gradient is applied where $G_R$ is a resultant of Gx and Gy gradients with the direction determined by the relative intensities of the components. This provides dispersion of the spins to give different resonance frequencies in a number of strips perpendicular to the direction of $G_R$. According to this example of the present invention the procedure only differs from that described in the said co-pending application in that the $G_R$ gradient is switched to give a line spectrum free induction decay (FID) resonance signal. Thus the spacing of the strips in the slice is enough to accommodate the chemical shift spectrum. This FID signal is Fourier Transformed to obtain line integrals corresponding to a particular chemical shift for each of the strips.

This procedure is repeated for a plurality of different orientations of strips in the slice, by changing the direction of the $G_R$ gradient and the convolution techniques known for computed tomography x-ray procedures (as described in application No. 22291/78) are used to provide a picture for each chemical shift of interest. As in the previous embodiment this is only a low resolution matrix.

Figure 5:
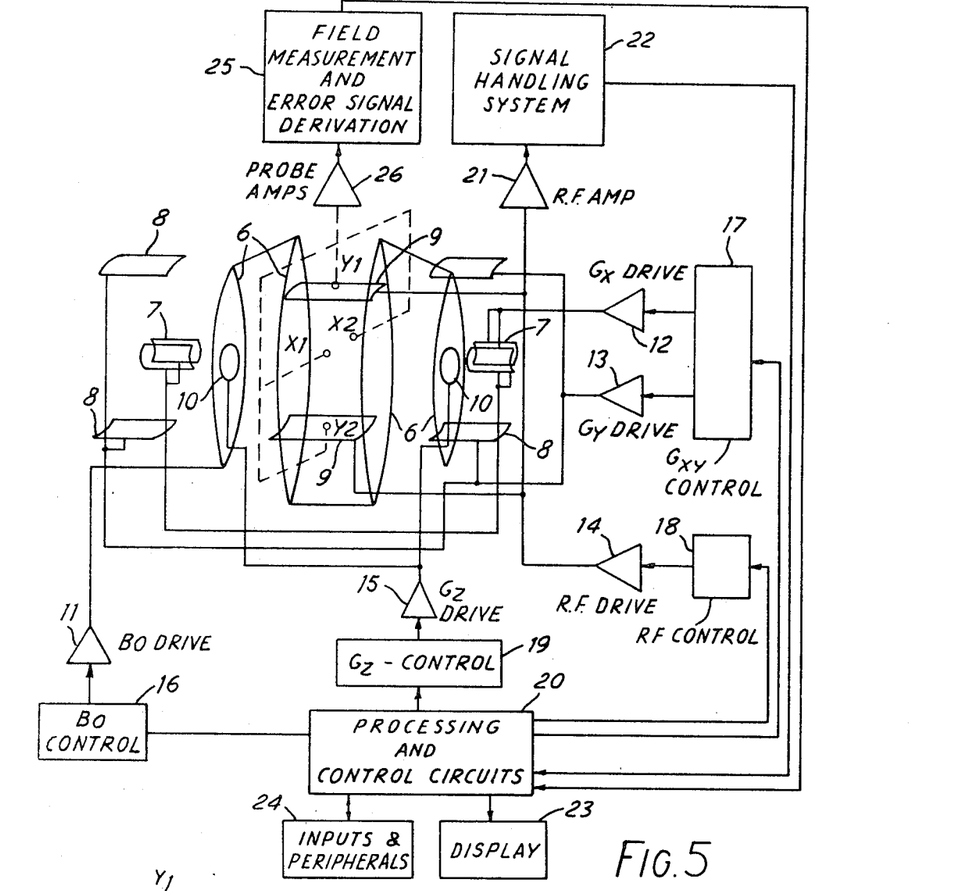
FIG. 5 shows an NMR imaging system which can be used for this invention.

The method described hereinbefore may be performed on a suitable NMR examining apparatus of which one example is shown in simplified form in FIG. 5. Illustrated schematically only are: coils 6, which provide the steady Bo field; 7, which provide the Gx field gradient; coils, 8 which provide the Gy field gradient; coils 9, which provide the RF fields; and coils 10, which provide the Gz field gradient. The coils are driven by Bo, Gx, Gy, RF and Gz drive amplifiers 11, 12, 13, 14 and 15 respectively, controlled by Bo, Gxy, RF and Gz control circuits 16, 17, 18 and 19 respectively. These circuits can take suitable forms which will be well known to those with experience of NMR equipment and other apparatus using coil induced magnetic fields. The circuits are controlled by a central processing and control unit 20 to achieve a desired pulse sequence such as that of this invention.

The FID signals sensed are received in this example by the RF coils 9 and are amplified by an RF amplifier 21 before being applied to signal handling circuits 22. In certain circumstances it may be preferable to provide separate coils specifically designed for the purpose, to sense the signal. The circuits 22 are arranged to make any appropriate calibrations and corrections but essentially transmit the signals to the processing circuits to provide the required representation of the examined slice. These circuits can conveniently be combined with the circuits which control the pulse sequence and thus are included in the circuits indicated at 20. The information thus obtained can be displayed on a display 23, such as a television monitor, and this may include inputs and other peripherals 24 for the provision of commands and instructions to the machine, or other forms of output.

Figure 6:
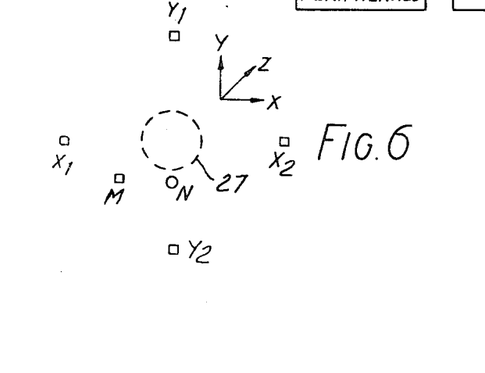
FIG. 6 shows a distribution of field sensing probes for the apparatus of FIG. 5.

The apparatus also includes field measurement and error signal circuits 25 which receive signals via amplifiers 26 from field probes $X_1$, $X_2$, $Y_1$, and $Y_2$, shown. The positions of the probes, in relation to the examined slice of the body 27 of the patient, are further shown in FIG. 6. $X_1$, $X_2$, $Y_1$ and $Y_2$ are in this example simply miniature cells of pure, or slightly doped water (such as a closed test tube) surrounded by a small coil. Preferably the water is doped to have a suitable value of $T_1$, relaxation time-constant. The probes give a reliable resonance of 4.26 kHz/Oe Other types of probe may be used as desired.

Figure 7A:
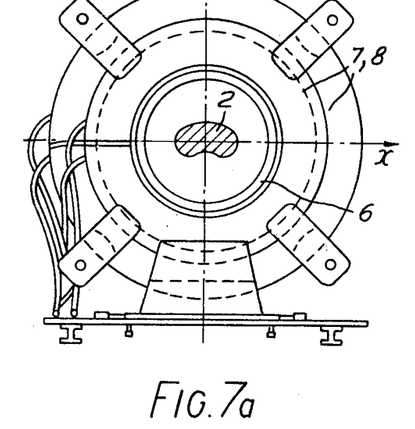
FIGS. 7a, 7b and 7c shows Bo and gradient field coils for this apparatus.
Figure 7B:
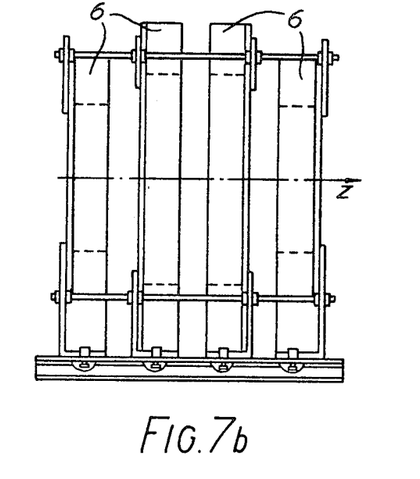

FIGS. 7a and 7b show in end and side elevation respectively a practical coil arrangement to provide the Bo field. FIG. 7a also shows the coils for production of the Gx and Gy field pulses and, to show approximate dimensions, the patient 27 in cross-section. The patient 27 is inserted in the tubular former of Gx and Gy coils 7, 8 and is supported there by a suitable couch or other supporting means. Such supports may be readily provided in any suitable form.

The coils 7, 8 are two sets of coils axially displaced, each set comprising two pairs of saddle coils, the pair 7 being at 90° to the pair 8. These coils are themselves inserted into the central aperture in Bo coils 6 which are wound in four parts connected in series to provide an approximately circular configuration which is well known to be desirable for production of a uniform field.

Figure 7C:
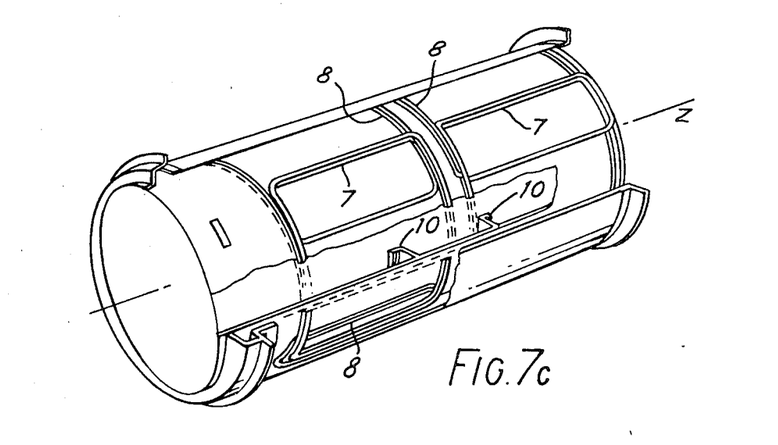

FIG. 7c is a partially cut-away perspective view which shows the coils 7, 8 in more detail. Also visible in the cut-away are the two circular coils 10 which provide the Gz field component for the gradient superimposed on Bo.

Figure 8:
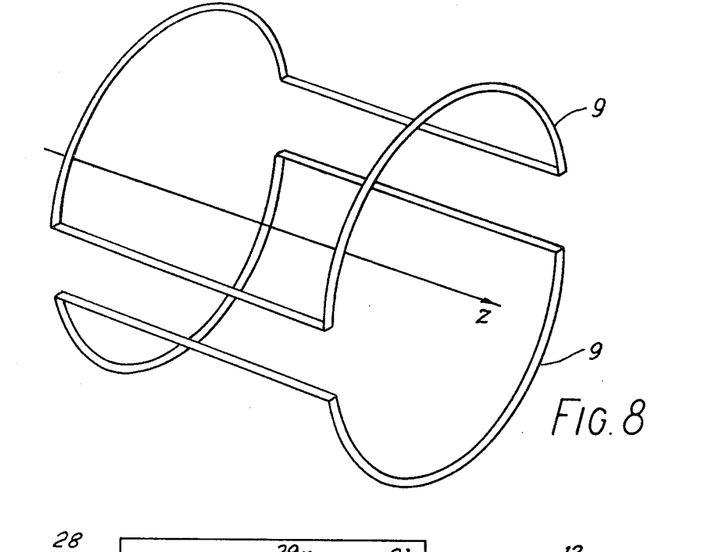
FIG. 8 shows RF coils for this apparatus.

The RF coils are shown in FIG. 8 in perspective. They are two saddle shaped coils 9 which are driven in parallel to provide the rotating RF field and which are in this example, also used to detect the FID signals which are of approximately the same frequency.

Figure 10:
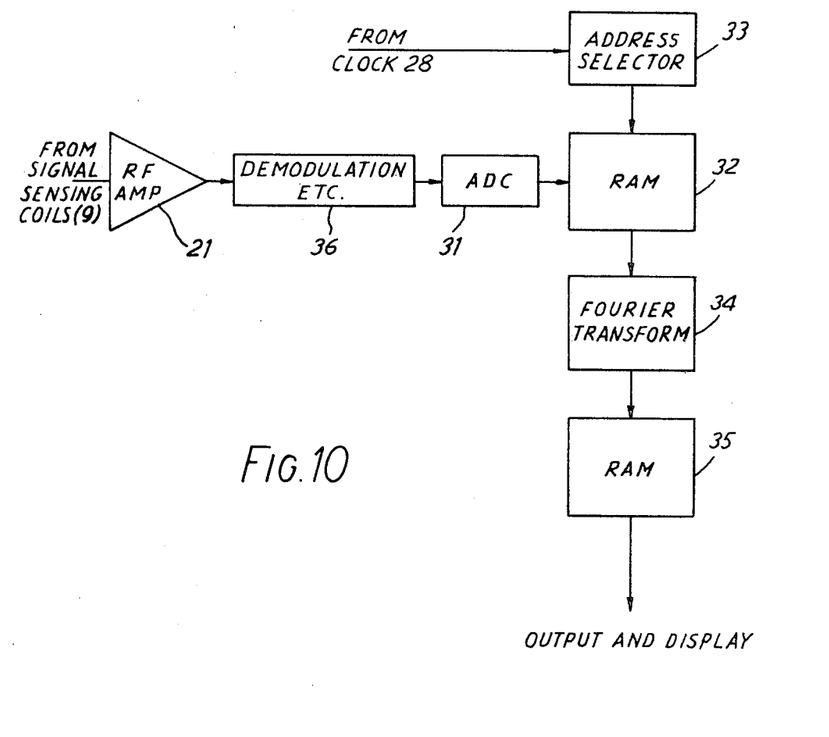
FIG. 10 shows a block diagrammatic circuit for processing the free induction decay and rephasing signals.

Further details of the coil winding will not be given since suitable coils can readily be devised, by those with the appropriate skills, to provide the fields required.

Where x, y and z gradients and RF fields are required in this apparatus, their predetermined amplitudes and directions are prestored in profile stores 29 shown in FIG. 10. The durations are in terms of a number of pulses of a system clock 28.

The operation of the four profile stores 29 is controlled by a sequence control store 30 which stores in similar manner a sequence of commands to operate the profile stores and the duration (number of clock pulses) of operation of each stage of the sequence, including gaps in the sequence. Stores 29 and 30 are conveniently programmable read only memories (PROM's).

Figure 9:
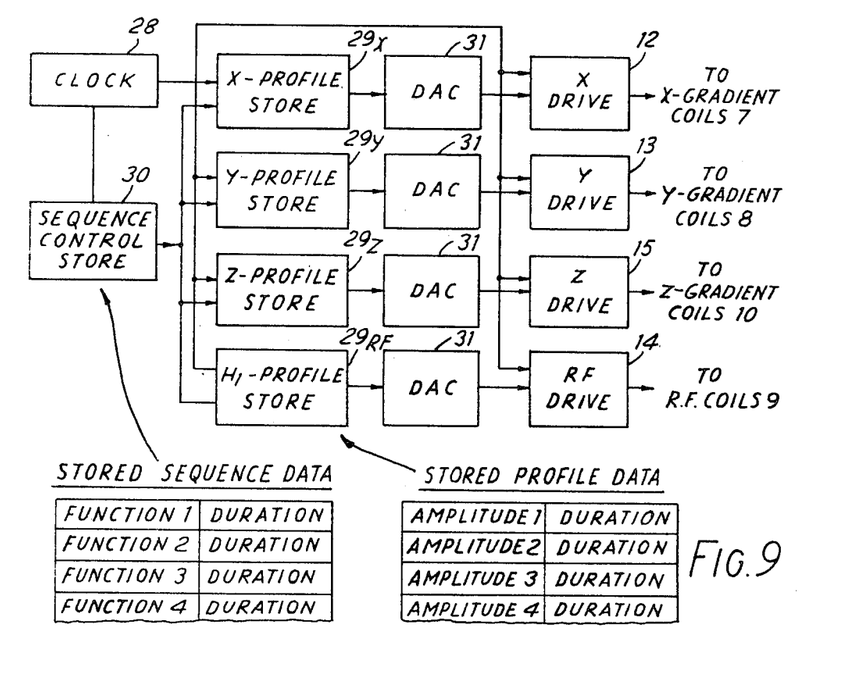
FIG. 9 shows circuits, in block form for applying the examining fields to the coils.

When commanded by a central (operator) control (which is shown in FIG. 9 but which may be associated with circuits 20) the sequence control store initiates the first pulse profiles. The appropriate stores 29 provide the amplitude and duration signals which are converted to analogue form in digital to analogue converters (DAC's) 31 and applied to respective coil drive circuits 12(x), 13(y), 14(RF) and 15(z). The respective drive circuits, which can take any form well known for driving field coils, provide the specified current to the appropriate coil for the specified duration.

The apparatus and circuits described so far may be adapted to provide different sequences of NMR examining pulses, by appropriately adjusting the stored sequence and profile data. Similarly other known NMR apparatus which are capable of applying a steady magnetic field, a pulsed RF field and Gx, Gy and Gz field gradients to a body, may be adapted in a manner straightforward to those skilled in the NMR art to apply the fields and pulse sequence described for this invention.

The basic features of the signal handling system are shown in FIG. 10. The FID signals from the signal sensing coils, in this example the RF coils 9, are amplified in an RF amplifier 21 demodulated and filtered before sampling in a unit 36 and applied via an analogue to digital converter (ADC) 31 to a store 32, such as a random access memory (RAM).

System clock pulses from the clock 28 are also applied to the RAM 32 to indicate the timing of the switched Gy (or $G_R$) pulse sequence causing the line spectrum FID's and hence the identities of the FID signals. The input and output from RAM store 32 is effected by a suitably preprogrammed address selector 33 using the system clock pulses for input timing.

The signals extracted from the RAM store 32 are processed by a Fourier Transform circuit 34 which operates in a well established manner. The processed data is held in another RAM store 35 in convenient form to be output for display.

Variations of the circuit given, for controlling the pulsed field gradients and for handling the FID signals, may readily be devised within the scope of this invention.

Furthermore it will be appreciated that there has been described one form of NMR imaging apparatus which may readily be used to examine chemical shifts as explained in this invention. However other imaging systems have been proposed and they may be adapted to implement this invention.

As an alternative to the procedure first described of selecting the strip by first saturating outside a slice and then applying a gradient therein, it is possible to apply simultaneously two orthogonal AC gradients in z and x directions. This is however not a preferred alternative. It will also be understood that the procedure explained for obtaining measurements for chemical shifts for phosphorus may be adapted to measurements for other chemicals by appropriate changes of frequency.

What we claim is:

1. A method of determining the distribution, in a body, of chemicals including a chosen element, the method including the steps of: exciting nuclear magnetic resonance for said element preferentially in a region in said body; applying a magnetic field having a gradient in said region to introduce a frequency dispersion in said resonance, said gradient being periodically reversed to provide free induction decay signals having a Fourier transform in the form of a line spectrum; measuring the free induction decay signals; and Fourier transforming the free induction decay signals to obtain an indication of chemical shifts of resonance excited for said elements for a plurality of individual parts of said region as dispersed spectra around the lines of said line spectrum.

2. A method according to claim 1 wherein the region in which resonance is excited is a strip in said body and the periodically reversed gradient is a gradient along said strip.

3. A method according to claim 2 wherein said steps are repeated to indicate chemical shifts for a plurality of individual parts along each of a plurality of said strips.

4. A method according to claim 1 wherein the region in which resonance is excited is a substantially planar slice of said body and the periodically reversed gradient is a gradient in a chosen direction in said slice to provide signals representing chemical shifts for a plurality of parallel strips perpendicular to said chosen direction.

5. A method according to claim 4 wherein the preceding steps are repeated for a plurality of directions of said gradient to provide signals representing chemical shifts for a plurality of sets of parallel strips at different orientation in the plane of said slice and said signals are further processed to provide an image of said planar slice for at least one of said chemical shifts.

6. A method of investigating the distribution of chemicals in a body, the method including the steps of: applying magnetic fields to cause nuclear magnetic resonance preferentially in a region of said body at a frequency appropriate to a chosen element; applying a periodically reversed magnetic field having a field gradient along said region to produce dispersion in said resonance, the timing of the periodically reversed magnetic field being such that the region is effectively divided into a plurality of smaller regions, the nuclei of the chosen element in each smaller region resonating within a unique frequency band, and dispersion in that band representing a chemical shift to be determined; sensing free induction decay and rephasing signals emitted by the nuclei as the field gradient is periodically reversed; sampling the free induction decay and rephasing signals and Fourier Transforming the samples so that the frequencies in the samples are dispersed, the dispersion being indicative of both spatial and chemical shift, the gradient being of sufficient amplitude that the spatial shift is larger than the chemical shift by an amount sufficient to avoid ambiguity.

7. A method of determining the distribution in a body of chemicals including a chosen element, the method including the steps of: applying a steady and substantially uniform magnetic field at least in a region of interest of said body; applying a first magnetic field having a first gradient in said region together with a pulse of RF energy tailored to saturate the spins of nuclei in the region with the exception of a substantially planar slice thereof perpendicular to the direction of the gradient; applying a second magnetic field having a second gradient in a direction in the slice together with an RF pulse sufficient to excite the nuclei in a strip therein; applying a third magnetic field having a third gradient in a direction orthogonal to the first and second gradients, said third gradient being periodically reversed to provide a line spectrum free induction decay signal representing free induction decays for a plurality of different locations along said line, such that the spacing of the lines of said spectrum is sufficient to accommodate the chemical shift spectrum of each location in the strip.

8. A method according to claim 7, including repeating said steps for each of a plurality of lines in said slice to provide chemical shifts for a matrix of said locations.

9. A method according to any one of claims 7 or 8, wherein said lines are excited by $p/2$ RF pulses.

10. A method of determining the distribution in a body of chemicals including a chosen element, the method including the steps of: applying a steady and uniform magnetic field at least in a region of interest of said body; applying a magnetic field having a gradient in said region together with a pulse of RF energy to excite to resonance nuclei in a substantially planar slice of said region of interest; applying a further magnetic field having a gradient in a chosen direction in said slice, the further magnetic field being periodically reversed to provide a line spectrum free induction decay signal representing a plurality of substantially parallel strips in said slice perpendicular to the chosen direction; Fourier Transforming the free induction decay signal to obtain line integrals of chemical shifts for each of said strips; repeating the preceding steps for a plurality of different directions, in the slice, of the gradient of the further magnetic field, and processing the line integrals for all of said directions to provide said distribution.

11. An apparatus for determining the distribution in a part of a body of chemicals including a chosen element, the apparatus comprising: means for exciting nuclear magnetic resonance for said element preferentially in a region of said body; means for applying a magnetic field having a gradient in said region to introduce a frequency dispersion in said resonance, said gradient being periodically reversed to provide free induction decay signals having a Fourier transform comprising a line spectrum; means for measuring the free induction decay signals to provide chemical shifts for said element for a plurality of individual parts of said region as dispersed spectra around the lines of said line spectrum.

12. An apparatus according to claim 11 wherein the means for exciting excites nuclear magnetic resonance in a strip in said body, and the means for applying the magnetic field having a gradient produces the gradient in the direction of the strip.

13. An apparatus according to claim 12 wherein the means for exciting excites a plurality of different strips.

14. An apparatus according to claim 11 wherein the means for exciting excites nuclear magnetic resonance in a substantially planar slice of said body; the means for applying a magnetic field provides a gradient in said slice for each of a plurality of directions thereof to provide signals representing chemical shifts for a plurality of parallel strips perpendicular to each of said directions; and wherein the apparatus further comprises means for processing the signals to provide an image of the planar slice for at least one of the chemical shifts.

* * * * *